United States Patent [19]

Sakuma

[11] Patent Number: 4,661,460

[45] Date of Patent: Apr. 28, 1987

[54] METHOD OF JUDGING IMMUNOLOGICAL REACTIONS

[75] Inventor: Hajime Sakuma, Hachioji, Japan

[73] Assignee: Olympus Optical Co., Ltd., Japan

[21] Appl. No.: 660,363

[22] Filed: Oct. 12, 1984

[30] Foreign Application Priority Data

Oct. 18, 1983 [JP] Japan .................................. 58-194858

[51] Int. Cl.$^4$ ...................... G01N 21/82; G01N 33/53
[52] U.S. Cl. ..................................... 436/165; 356/246;
422/73; 422/102; 436/533; 436/534; 436/805
[58] Field of Search .................. 436/43, 164, 165, 69,
436/518, 519, 520, 533, 534, 805, 807, 808, 809,
810; 422/73, 102; 73/64.1; 356/246

[56] References Cited

U.S. PATENT DOCUMENTS

| | | | |
|---|---|---|---|
| 4,197,088 | 4/1980 | Meserol et al. | 422/104 X |
| 4,290,997 | 9/1981 | Suovaniemi | 422/73 |
| 4,303,616 | 12/1981 | Kano et al. | 422/73 X |
| 4,373,931 | 2/1983 | Takekawa | 422/73 X |
| 4,436,827 | 3/1984 | Tamagawa | 422/73 X |
| 4,447,396 | 5/1984 | Kano | 422/73 |
| 4,452,759 | 6/1984 | Takekawa | 422/73 |
| 4,466,740 | 8/1984 | Kano et al. | 422/73 X |
| 4,556,641 | 12/1985 | Kano et al. | 436/805 X |
| 4,563,430 | 1/1986 | Kano et al. | 436/805 X |
| 4,566,791 | 1/1986 | Goldsmith | 356/246 |

FOREIGN PATENT DOCUMENTS

| | | | |
|---|---|---|---|
| 0002559 | 1/1981 | Japan | 422/73 |
| 0002561 | 1/1981 | Japan | 422/73 |
| 0002564 | 1/1981 | Japan | 422/73 |
| 0208439 | 12/1982 | Japan | 422/73 |

Primary Examiner—Barry S. Richman
Assistant Examiner—Robert J. Hill, Jr.
Attorney, Agent, or Firm—Parkhurst & Oliff

[57] ABSTRACT

A sample and a reagent are delivered into a reaction vessel having a plurality of inclined bottom surface portions, inclination angles of these portions being increased in a step-wise manner. The reaction vessel is kept still for such a time period that particles descend on the bottom surface portions to from particle patterns. The particle patterns thus formed on respective bottom surface portions are separately detected to produce agglutination and non-agglutination signals. The antigen-antibody reaction is judged in accordance with the agglutination and non-agglutination signals.

10 Claims, 24 Drawing Figures

| Bottom Shape of Reaction Vessel | Agglutination Pattern | Intermediate Agglutination Pattern | Non-Agglutination Pattern |
|---|---|---|---|
| ⌴ | ● | ⊙ | ⊙ |
| ⌴ | ● | ⊙ | ⊙ |

FIG_3
PRIOR ART

FIG_4

FIG_10A

FIG_10B

FIG_10C

FIG_10D

FIG_10E

FIG_10F   "1"   "1"   "0"   "0"

METHOD OF JUDGING IMMUNOLOGICAL REACTIONS

BACKGROUND OF THE INVENTION

The present invention relates to a method of judging of an immunological reaction, i.e. an antigen-antibody reaction by detecting a pattern formed by particles descending on an inclined bottom surface of a reaction vessel, and also relates to a reaction vessel for use in such a method.

Heretofore, it has been known to judge or determine the antigen-antibody reaction by deliverying an antigen or antibody sample and an antibody or antigen reagent into a reaction vessel having an inclined bottom surface, and then detecting a pattern formed by particles descending on the inclined bottom surface. When there is an antigen-antibody reaction, particles are agglutinated and are deposited uniformly on the inclined bottom surface like snow to form an agglutination pattern. In contrast, when an antigen-antibody reaction does not occur, the particles are not agglutinated and roll down along the inclined bottom surface into the lowermost portion of the reaction vessel to form a non-agglutination pattern.

Figure 1A:
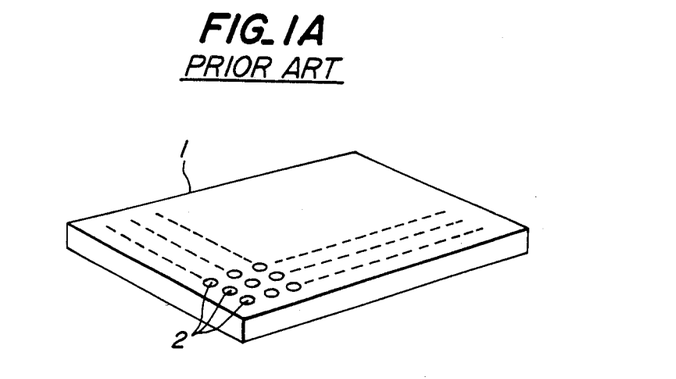
FIGS. 1A, 1B and 1C show the construction of a reaction vessel used in a known method.
Figure 1B:
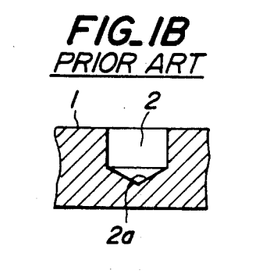
Figure 1C:
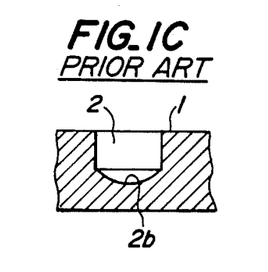
Figure 2:
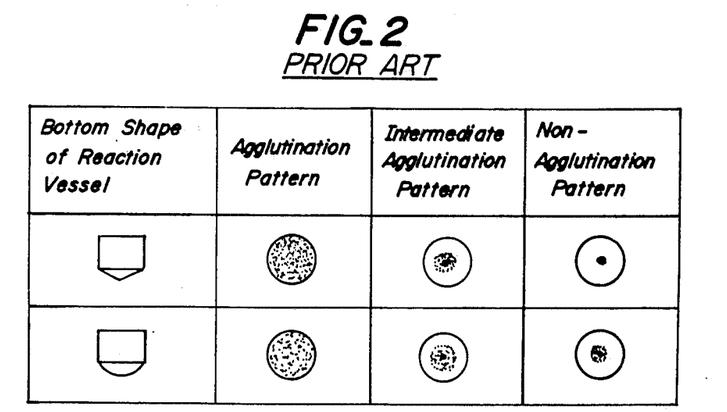
FIG. 2 illustrates various particle patterns formed on the reaction vessel in the known method.

FIG. 1A illustrates a construction of a microplate 1 which has been used in the known method. The microplate 1 comprises a transparent plate like substrate and a number of reaction vessels 2 formed by depressions arranged in one major surface of the substrate in a matrix form. Each reaction vessel 2 has a conically shaped inclined bottom surface 2a as illustrated in a cross section of FIG. 1B. The reaction vessel 2 may have a round concave bottom surface 2b as illustrated in FIG. 1C. After delivering a sample and a reagent into such a reaction vessel 2, the reaction vessel 2 is kept still for a given time period. Then on the inclined bottom surface of reaction vessel 2 there is formed the agglutinated particle pattern or non-agglutinated particle pattern by means of the particles descending on the bottom surface. Several examples of such particle patterns are depicted in FIG. 2. If an antigen-antibody reaction has taken place in the reaction vessel 2, the particles are agglutinated and are deposited uniformly on the inclined bottom surface. But if a antigen-antibody reaction has not occurred, the particles are not agglutinated with each other and roll down along the inclined bottom surface into the lowermost portion, i.e. the center of the conically inclined bottom surface. Therefore, by detecting the particle pattern formed on the bottom surface of a reaction vessel, it is possible to judge whether or not an antigen-antibody reaction has occurred. However, in the known method, it is difficult to accurately detect intermediate aggutination patterns between the possitively agglutinated particle pattern and non-agglutinated particle pattern, due to weak agglutination. Therefore, in the known method it is only possible to judge whether the agglutination has occurred or the agglutination has not occurred.

When checking HB, syphilis, etc., it is necessary to obtain information or data about the degree of agglutination, i.e. the agglutination power, in addition to judging whether the aglutination has occurred or not. Further, some blood subtypes have agglutination powers which differ from one another only slightly. Therefore, in a blood subtype test, there might be misjudgement. Moreover, when detecting the particle pattern photoelectrically, such slightly different particle patterns could not be judged precisely.

Figure 3:
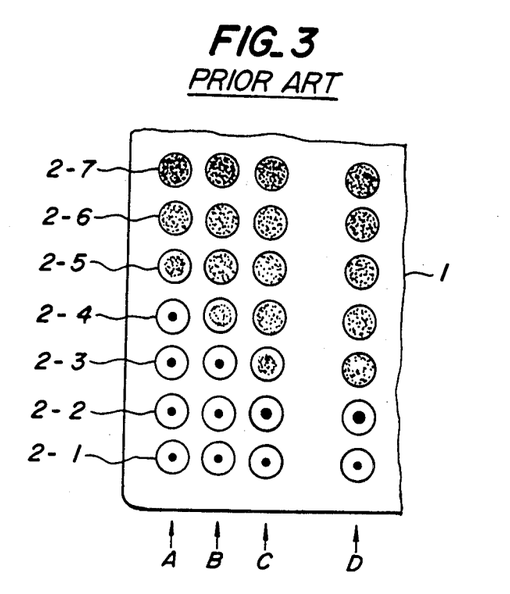
FIG. 3 is a plan view depicting particle patterns formed on bottom surfaces of reaction vessels of a microplate in another known method.

In a known method of detecting the agglutination power a sample is diluted by factors of two, four, eight . . . times successively by means of a microtiter to prepare a plurality of diluted samples having different concentrations. Then these differently diluted samples are delivered into successive reaction vessels 2-1, 2-2, 2-3 . . . formed in the microplate 1 as shown in FIG. 3. That is to say, seven diluted samples of a first sample are delivered into seven reaction vessels of a first column A, seven diluted samples of a second sample are delivered into seven reaction vessels of a second column B and so on. At the same time, into seven reaction vessels of a column D are delivered seven diluted samples of a standard sample whose agglutination power is known. After a given time period, particle patterns formed on the bottom surfaces of reaction vessels 2-1, 2-2 . . . 2-7 are compared with standard particle patterns formed on the bottom surfaces of reaction vessels belonging to the column D. In this manner, values or indices of the agglutination power of unknown samples can be detected. In this method, even if the agglutination power is relatively small, the judgement can be effected precisely. However, in the known method, since it is necessary to deliver the differently diluted samples into the reaction vessels, the process could not be carried out efficiently. Particularly, if the concentrations of the diluted samples are not correct, judging accuracy is greatly affected resulting in a decrease of reliability. Further, the method requires inherently larger amounts of sample and reagent, and thus the running cost is liable to be increased.

SUMMARY OF THE INVENTION

The present invention has for its object to provide a novel and useful method of detecting an antigen-antibody reaction, which method can obviate the various drawbacks of the known methods, which can judge the intermediate particle patterns precisely and which can detect weak agglutinations reliably.

According to the invention, a method of judging an immunoligical reaction by detecting an agglutination or non-agglutination pattern formed by particles descending upon an inclined bottom surface of a reaction vessel comprises delivering a sample and a reagent into a reaction vessel having a plurality of inclined bottom surface portions, inclination angles of the bottom surface portions with respect to the horizontal plane being increased in a step-wise manner;

keeping the reaction vessel substantially still for such a time period that almost all particles descend on the bottom surface portions of the reaction vessel to form particle patterns thereon;

detecting separately the particle patterns formed on respective bottom surface portions to produce a plurality of agglutination and non-agllutination signals; and judging the antigen-antibody reaction on the basis of the plurality of agglutination and non-agglutination signals.

The present invention also has for its object to provide a reaction vessel for use in the above method according to the invention.

According to the invention, a reaction vessel for use in a method of judging an immunological reaction by detecting an agglutination or non-agglutination pattern formed by particles descending upon an inclined bottom surface of a reaction vessel comprises a plurality of inclined bottom surface portions, inclination angles of these bottom surface portions being increased in a step-wise manner.

DESCRIPTION OF THE PREFERRED EMBODIMENTS

Figure 4:
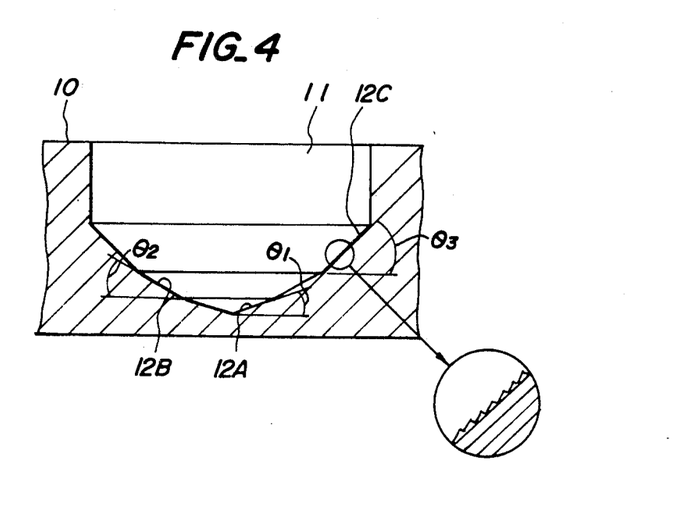
FIG. 4 is a cross sectional view illustrating an embodiment of the reaction vessel used in the method according to the invention.

FIG. 4 is a cross sectional view showing an embodiment of the reaction vessel for use in the judging method according to the invention. In the present embodiment, a number of reaction vessels 11 are formed in a microplate 10 and each reaction vessel has a bottom surface consisting of three inclined portions 12A, 12B and 12C whose inclination angles $\theta_1$, $\theta_2$ and $\theta_3$ with respect to the horizontal plane are successively increased in a step-wise manner. That is to say, $\theta_1 < \theta_2 < \theta_3$. In these inclined bottom surface portions 12A, 12B and 12C there are formed a number of fine steps or grooves as illustrated in an enlarged manner at right lower part of FIG. 4. These steps contribute to form a stable base layer for particles descending upon the bottom surface.

Figure 5A:
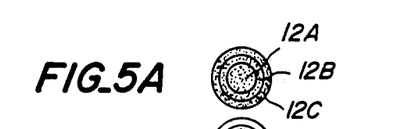
FIGS. 5A to 5D are plan views showing particle patterns formed by the method according to the invention.
Figure 5B:
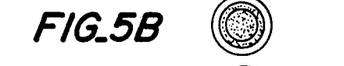
Figure 5C:
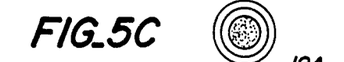
Figure 5D:
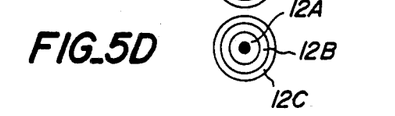

FIGS. 5A to 5D are plan views showing agglutination and non-agglutination patterns formed on the bottom surface of the reaction vessel 11 illustrated in FIG. 4. FIGS. 5A to 5C depict agglutination patterns having different agglutination powers. The agglutination pattern shown in FIG. 5A shows the largest agglutination power, in which particles are deposited uniformly up to the outermost bottom surface portion 12C having the largest inclination angle $\theta_3$. In the intermediate agglunation pattern illustrated in FIG. 5B, particles are not deposited on the portion 12C, but are uniformly deposited on the remaining portions 12A and 12B having the inclination angles $\theta_1$ and $\theta_2$ smaller than $\theta_3$. FIG. 5C depicts the very weak agglutination pattern in which particles are uniformly deposited only on the innermost bottom portion 12A having the smallest inclination angle $\theta_1$. FIG. 5D shows a non-agglutination pattern and almost all particles are collected at the lowermost center of the bottom surface and no uniformly deposited particle pattern is formed on any bottom surface portions 12A, 12B and 12C. Therefore, according to the invention, by detecting on which bottom surface portions are formed uniformly deposited particle patterns, it is possible to analyze the agglutination quantitatively so as to judge the degree of the agglutination power.

Figure 6:
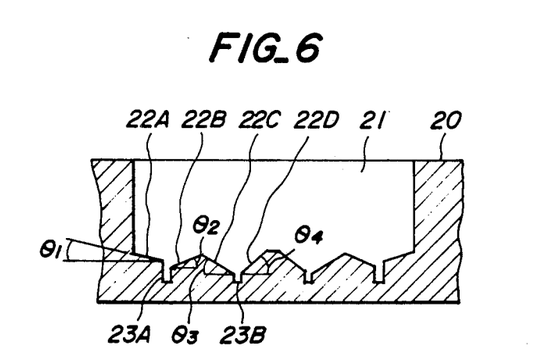
FIG. 6 is a cross sectional view showing another embodiment of the reaction vessel used in the method according to the invention.

FIG. 6 is a cross sectional view showing another embodiment of a reaction vessel for use in the method according to the invention. In this embodiment, in a microplate 20 are formed a number of reaction vessels 21, each of which has four inclined bottom surface portions 22A to 22D and two ring-shaped grooves 23A and 23B. The bottom portions 22A and 22C are inclined inwardly by angles $\theta_1$ and $\theta_3$, respectively and the bottom portions 22B and 22D are inclined outwardly by angles $\theta_2$ and $\theta_4$, respectively. The groove 23A is formed between the bottom portions 22A and 22B and the groove 23B is formed between the bottom portions 22C and 22D. The inclination angles $\theta_1$ to $\theta_4$ are increased in order in a step-wise manner, i.e. $\theta_1 < \theta_2 < \theta_3 < \theta_4$. It should be noted that the bottom surface portions 22A to 22D have fine steps or grooves formed therein so as to be able to form a stable base layer for particles.

Figure 7A:
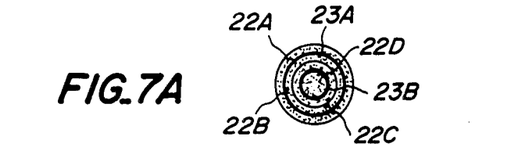
FIGS. 7A to 7E are plan views illustrating particle patterns formed on the reaction vessel shown in FIG. 6.
Figure 7B:
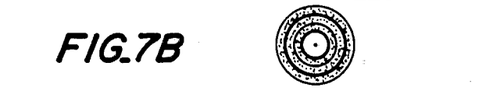
Figure 7C:
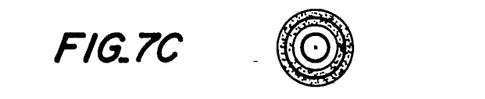
Figure 7D:
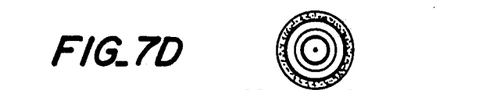
Figure 7E:
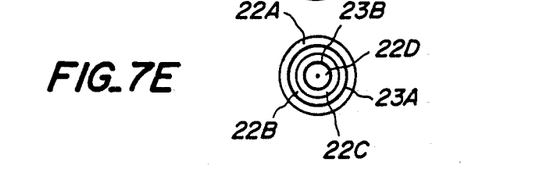

FIGS. 7A to 7E show agglutinated and non-agglutinated particle patterns formed on the bottom surface of reaction vessel 21 shown in FIG. 6. FIGS. 7A to 7D illustrate agglutination patterns having different agglutination powers which are successively decreased. FIG. 7E shows a non-agglutination pattern in which almost all particles roll down along the inclined bottom surface portions 22A to 22D into the grooves 23A and 23B, so that no uniformly deposited particle pattern is formed on any bottom portions 22A and 22D. In the present embodiment, even when agglutination patterns are formed, some particles fall into the grooves 23A and 23B, so that the grooves can be seen or detected clearly. Therefore, the particle pattern can be positively judged with the naked eye. Particularly, in the case of detecting the particle pattern photoelectrically, the patterns formed on each bottom surface portions 22A to 22D can be easily and precisely distinguished from each other, and therefore a judgement can be effected much more accurately.

Figure 8:
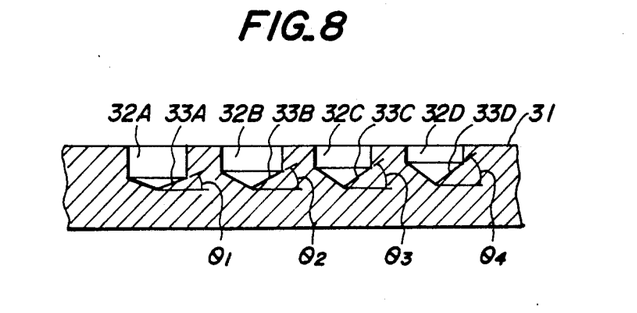
FIG. 8 is a cross sectional view depicting still another embodiment of the reaction vessel used in the method according to the invention.

FIG. 8 is a cross sectional view showing still another embodiment of the reaction vessel for use in the method according to the invention. In the embodiment illustrated in FIG. 6, in each reaction vessel there are formed a plurality of bottom portions whose inclination angles differ from each other in a step-wise manner. In the present embodiment, these bottom portions are formed in different reaction vessels. That is to say, in a microplate 31 there are formed a plurality of reaction vessels 32A, 32B, 32C and 32D having inclined bottom surfaces 33A, 33B, 33C and 33D, respectively, and inclination angles $\theta_1$, $\theta_2$, $\theta_3$ and $\theta_4$ of these bottom surfaces with respect to the horizontal plane are successively increased in a step-wise manner. In these reaction vessels 32A to 32D are delivered given amounts of sample and reagent. It should be noted that the samples delivered into these reaction vessels have the same concentration. Therefore, the delivery of the sample can be carried out very simply and no measuring error is produced due to possible variation in concentrations as compared with the known method explained with reference to FIG. 3.

Figure 9:
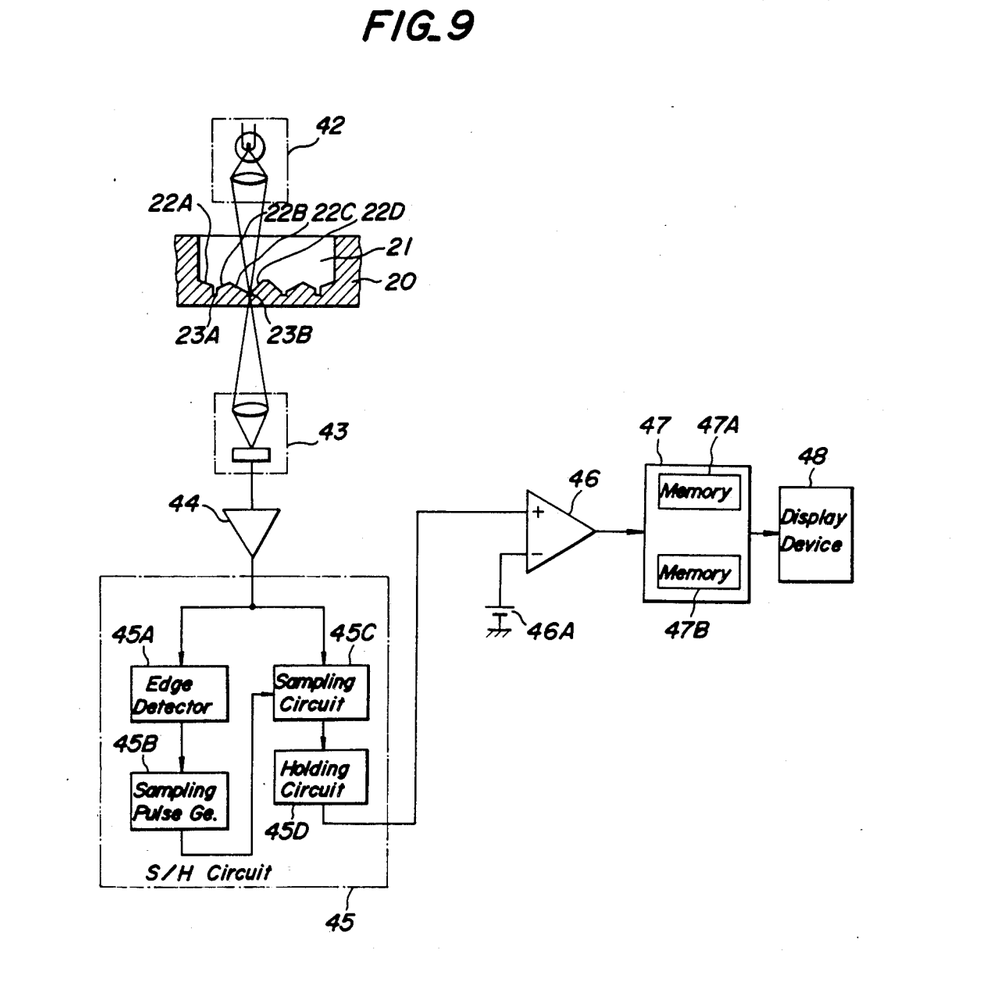
FIG. 9 is a schematic view showing an embodiment of an apparatus for carrying out the method according to the invention.

FIG. 9 is a schematic diagram showing an embodiment of the apparatus for carrying out the judging method according to the invention which uses the reaction vessel illustrated in FIG. 6. The microplate 20 having a number of reaction vessels 21 are successively transported through a photoelectrically detecting position by means of a suitable transporting mechanism such as a roller carrier and a belt carrier. At the photoelectrically detecting position there are arranged a light source 42 and a photoelectric detector 43 above and below the microplate 20, respectively. By means of the light source 42 and photoelectric detector 43, the particle pattern formed on the bottom surface of the reaction vessel 21 is photoelectrically detected. An output signal from the detector 43 is amplified by an amplifier 44 and then is supplied to a sample and hold circuit 45 in which, from the input detection signal, pattern signals are derived representing the particle patterns formed on respective inclined bottom portions 22A to 22D with the aid of signals corresponding to the grooves 23A and 23B. Then the pattern signals thus extracted are successively supplied to a comparator 46 and are compared with a threshold value given by a reference D.C. voltage supply source 46A. The comparator 46 produces output signals representing agglutination or non-agglutination. These output signals may be logic "1" or "0" signal.

Figure 10A:
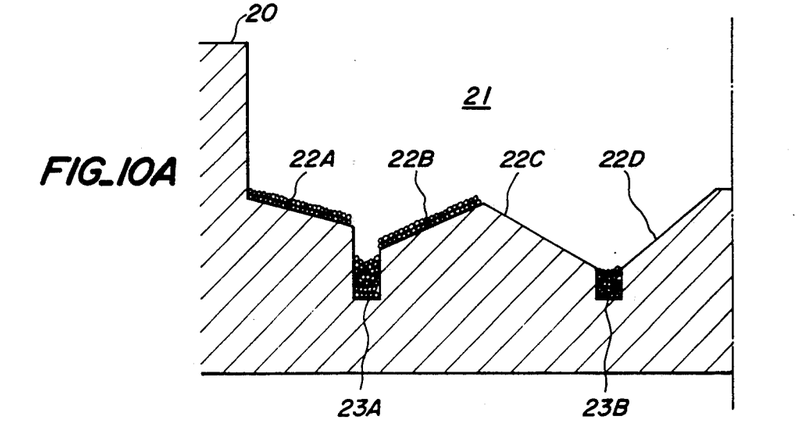
FIGS. 10A to 10F show the reaction vessel and signal waveforms for explaining the operation of the apparatus illustrated in FIG. 9.
Figure 10B:
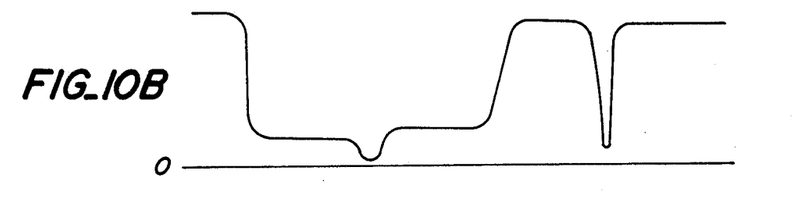
Figure 10C:
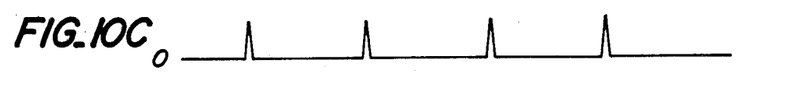
Figure 10D:
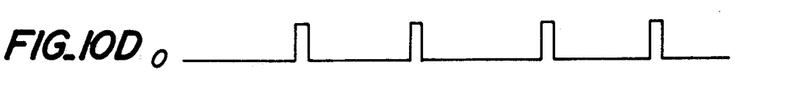
Figure 10E:
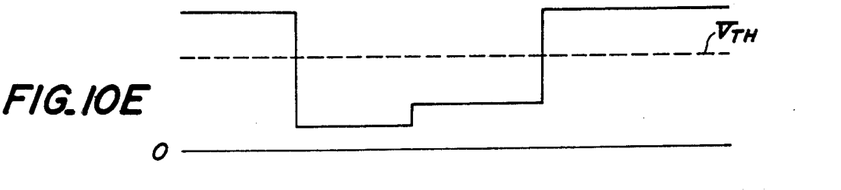
Figure 10F:
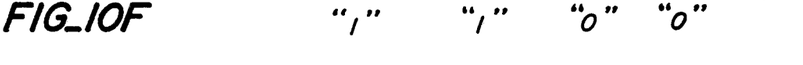

Now the detailed construction and operation of the sample and hold circuit 45 and comparator 46 will be explained with reference to FIGS. 10A to 10F. FIG. 10A shows a cross section of a left hand half of the reaction vessel 21 and FIG. 10B is a waveform of the detection signal supplied from the amplifier 44. As shown in FIG. 10A, the uniformly deposited particle patterns are formed only on the bottom portions 22A and 22B. That is to say, this pattern corresponds to the intermediate pattern illustrate in FIG. 7C. The sample and hold circuit comprises an edge detector 45A for detecting steep edges of the detection signal shown in FIG. 10B to produce an edge signal illustrated in FIG. 10C. The edge signal thus detected is supplied to a sampling pulse generator 45B to produce a sampling pulse shown in FIG. 10D. The sampling pulse has a timing with respect to a related edge pulse such that the detection signal can be sampled at a predetermined time, for instance, at a center position of an inclined bottom surface portion, following a corresponding edge pulse. Such a sampling pulse may be generated by delaying the edge pulse by a predetermined time period. The sampling pulse is supplied to a sampling circuit 45C to sample the input detection signal to produce a sampled signal which is then stored in a holding circuit 45D. FIG. 10E shows an output signal of the holding circuit 45D which forms the pattern signals. Then by comparing these pattern signals with the threshold level $V_{TH}$ in the comparator 46, it is possible to detect the agglutination (logic "1") and the non-agglutination (logic "0") in an accurate manner as shown in FIG. 10F.

The logic signal representing the agglutination and non-agglutination is supplied to a judging circuit 47. In the judging circuit 47 there are provided a pair of memories 47A and 47B in each of which the pattern signals for the bottom portions 23A to 23D can be stored. At first, standard particle patterns are formed by using several standard samples having known agglutination powers. Then the pattern signals for the bottom surface portions 23A to 23D are derived and stored in the memory 47A. Then a sample to be tested is delivered into the reaction vessel together with a reagent and particle patterns formed on the portions 22A to 22D are detected and stored in the memory 47B. In the judging circuit 47, the agglutination power of the sample is derived by comparing the pattern signals stored in the memories 47A and 47B. The thus derived agglutination power is supplied to a display device 48.

The present invention is not limited to the embodiments so far explained, but many modifications and alternations can be conceived by those skilled in the art and are within the scope of the invention. For instance, the method according to the invention could be carried out by any apparatus other than that shown in FIG. 9. Further, the particle patterns formed on the inclined bottom portions may be judged with the naked eye. In the above embodiments, the reaction vessels are formed in a microplate, but they may be constructed as separate containers.

In the method according to the invention, the sample having a given constant concentration and reagent are delivered into the reaction vessel having a plurality of inclined bottom portions whose inclination angles are different from each other and the particle patterns formed on these bottom portions are detected separately, any measuring error is not introduced due to possible variation of the concentration of the sample, and therefore it is possible to effect accurate judgement. Further, since the inclination angles of the bottom portions are successively increased in a step-wise manner, the intermediate particle patterns can be clearly distinguished from one another and thus the pattern detection can be performed precisely. Therefore, the agglutination power can be accurately detected and weak agglutination can also be clearly judged. Moreover, in the case of testing each samples by using respective reaction vessels having inclined bottom surface portions as illustrated in FIGS. 4 and 6, amounts of sample and reagent can be saved to a great extent and the running cost can be reduced materially.

What is claimed is:

1. A method of judging the existance and extent of an immunological reaction between a sample and a reagent by detecting an agglutination or non-agglutination pattern formed by particles descending upon an inclined bottom surface of a reaction vessel comprising:

delivering the sample and the reagent into a reaction vessel having a plurality of discrete substantially flat bottom surface portions, inclination angles of the substantially flat bottom surface portions with respect to a horizontal plane being different from each other, each bottom surface portion including fine steps suitable for forming a stable base layer for descending particles;

keeping the reaction vessel substantially still for such a time period that substantially all particles descend on the substantially flat bottom surface portions of the reaction vessel to form a plurality of particle patterns thereon;

separately detecting the particle patterns formed on respective substantially flat bottom surface portions to produce a plurality of individual agglutination and non-agglutination signals, each signal corresponding to a respective flat bottom surface portion; and judging the existance and extent of immunological reaction between the sample and reagent on the basis of said plurality of agglutination and non-agglutination signals.

2. A method according to claim 1, wherein the reaction vessel was at least one groove formed between adjacent bottom surface portions.

3. A method according to claim 1, wherein said judging step comprises:
   storing a plurality of agglutination and non-agglutination signals of a standard sample whose agglutination power is known; and
   comparing the plurality of agglutination and non-agglutination signals of the sample with said stored agglutination and non-agglutination signals of the standard sample.

4. A method according to claim 1, wherein the particle patterns formed on the bottom surface portions are photoelectrically detected.

5. A method according to claim 4, wherein the particle patterns formed on the bottom surface portions are photoelectrically detected by moving the reaction vessel through a photoelectrically detecting position at which a light source and a photoelectric detector are arranged whereby a light beam emitted from the light source is transmitted through the reaction vessel and received by the photoelectric detector to produce a detection signal.

6. A method according to claim 5, wherein said plurality of agglutination and non-agglutination signals are derived by comparing the detection signal with a threshold value.

7. A method according to claim 6, wherein said detection signal is sampled at timings corresponding to alignment of respective center portions of respective surface bottom portions with the detection position, and successively sampled values are compared with the threshold value to produce logic signals as the agglutination and non-agglutination signals.

8. A method of judging the existance and extent of an immunological reaction between a sample and a reagent by detecting an agglutination or non-agglutination pattern formed by particles descending upon inclined bottom surfaces of a plurality of reaction vessels comprising:
   delivering the sample and the reagent into a plurality of discrete reaction vessels each having a substantially flat bottom surface, inclination angles of the flat bottom surface of adjacent reaction vessels with respect to a horizontal plane being different from each other, each bottom surface including fine steps suitable for forming a stable base layer for descending particles;
   keeping the reaction vessels substantially still for such a time period that substantially all particles descend on the substantially flat bottom surface of each of said reaction vessels to form a plurality of particle patterns thereon;
   separately detecting the particle patterns fomed on the substantially flat bottom surface of each of said adjacent reaction vessels to produce a plurality of individual agglutination and non-agglutination signals, each signal corresponding to the flat bottom surface of a respective reaction vessel; and
   judging the existance and extent of immunological reaction between the sample and reagent on the basis of said plurality of agglutination and non-agglutination signals.

9. A method according to claim 8, wherein the particle patterns formed on the bottom surfaces of said reaction vessels are photoelectrically detected.

10. A method according to claim 9, wherein said judging step comprises:
   storing a plurality of agglutination and non-agglutination signals of a standard sample whose agglutination power is known; and
   comparing the plurality of agglutination and non-agglutination signals of the sample with said stored agglutination and non-agglutination signals of the standard sample.

* * * * *